US005639733A

United States Patent [19]
Koike et al.

[11] Patent Number: 5,639,733
[45] Date of Patent: Jun. 17, 1997

[54] ALKYL GLYCOSIDE AQUEOUS SOLUTION

[75] Inventors: Toyomi Koike; Hiroshi Nagumo; Akira Yamamuro, all of Wakayama; Yukinaga Yokota, Osaka, all of Japan

[73] Assignee: Kao Corporation, Tokyo, Japan

[21] Appl. No.: 340,351

[22] Filed: Nov. 14, 1994

Related U.S. Application Data

[63] Continuation of Ser. No. 207,252, Mar. 8, 1994, abandoned, which is a continuation of Ser. No. 883,679, May 15, 1992, abandoned.

[30] Foreign Application Priority Data

May 16, 1991 [JP] Japan ................................. 3-111589

[51] Int. Cl.$^6$ ............... A61K 31/70; A01N 43/04; C07G 3/00; C07H 15/04
[52] U.S. Cl. ............ 514/25; 536/4.1; 536/18.5; 536/120
[58] Field of Search ................. 514/25; 536/4.1, 536/120, 18.5

[56] References Cited

U.S. PATENT DOCUMENTS

| | | | |
|---|---|---|---|
| 4,557,729 | 12/1985 | McDaniel et al. | 536/18.5 |
| 4,888,325 | 12/1989 | Schroeder et al. | 536/1.11 |
| 4,920,100 | 4/1990 | Lehmann et al. | 514/23 |

FOREIGN PATENT DOCUMENTS

| | | |
|---|---|---|
| 0301298 | 2/1989 | European Pat. Off. . |
| 0377883 | 7/1990 | European Pat. Off. . |

OTHER PUBLICATIONS

Database WPI, Derwent Publications, AN-92-168001, Patent Infomation-DE 4035722, May 14, 1992.
Database WPI, Derwent Publications, AN-87-349549, Patent Infomation-DE 3619375, Dec. 10, 1987.

*Primary Examiner*—John Kight
*Assistant Examiner*—Everett White
*Attorney, Agent, or Firm*—Oblon, Spivak, McClelland, Maier & Neustadt, P.C.

[57] ABSTRACT

Alkyl glycoside aqueous solutions, which satisfy the following conditions (a) and/or (b):

(a) the solution is maintained at a pH value exceeding 7, and
(b) the solution contains a water-soluble alcohol, are highly stable with respect to microbial activities, such as putrefaction and fungal growth, and are useful as surface active agents.

16 Claims, No Drawings

ALKYL GLYCOSIDE AQUEOUS SOLUTION

BACKGROUND OF THE INVENTION

This is a Continuation of application Ser. No. 08/207,252 filed on Mar. 8, 1994, now abandoned, which is a continuation of application Ser. No. 07/883,679 filed on May 15, 1992 abandoned.

FIELD OF THE INVENTION

The present invention relates to alkyl glycoside aqueous solutions which are highly stable to microbial degradation and are useful as surface active agents.

DISCUSSION OF THE BACKGROUND

Alkyl glycosides are low-irritant surface-active agents of the sugar-derivative type having excellent biodegradation capacity. In spite of their nonionic nature, they generate stable foams and exert action on other anionic surface active agents as a foam stabilizer. Because of these excellent properties, alkyl glycosides have been widely used as base materials in household detergents.

Alkyl glycosides are synthesized by a process in which a sugar is directly reacted with a higher alcohol in the presence of an acid catalyst (JP-A-59-139397 corresponding to U.S. Pat. No. 4,923,976, European Patent No. 0,132,043) or by a process in which a sugar is reacted first with a lower alcohol such as butanol to obtain a lower alkyl glycoside which is then reacted with a higher alcohol (JP-A-64-71895 corresponding to U.S. Pat. No. 4,990,605, JP-A-64-71896 corresponding to U.S. Pat. No. 4,898,934, JP-A-64-71897 corresponding to U.S. Pat. No. 4,847,368). (The term "JP-A" as used herein means an "unexamined published Japanese patent application)

Since alkyl glycosides have sugar skeletons in their structures, they are useful as surface active agents which satisfy the current trend toward the use of natural materials which are environmentally safe. Opposed to such utility, however, they suffer from the disadvantage that their aqueous solutions are apt to give rise to microbial propagation.

The prevention of putrefaction and fungal growth in surface active agents has been achieved by the addition of antiseptic and fungicidal agents which include, for example, (a) para-hydroxybenzoic acid esters such as methyl para-hydroxybenzoate, ethyl para-hydroxybenzoate and the like; (b) benzoic acids such as benzoic acid, sodium benzoate and the like; and (c) isothiazoles such as 1,2-benzisothiazoline-3-one and the like.

However, para-hydroxybenzoic acid esters have low solubility in water and are incorporated into micelles of surface active agents in emulsions, thus resulting in an insufficient effect against microorganisms in the water layers. As for benzoic acids, they are effective only within the acidic pH range and therefore are not suitable for the antiseptic and fungicidal treatments of alkyl glycosides. What is more important, the amounts of these two types of compounds which can be incorporated into products are limited from the viewpoint of safety.

In addition, isothiazoles are expensive and therefore cannot be used in cosmetics.

Thus, great concern has been directed toward the development of an effective method to protect alkyl glycoside aqueous solutions from putrefaction and fungal growth, and there remains a need for methods and compositions which overcome this problem.

SUMMARY OF THE INVENTION

Accordingly, it is an object of the present invention to provide an alkyl glycoside aqueous solution which has excellent stability to microbial activities and therefore can overcome the aforementioned problems involved in the prior art.

It is another object of the present method to provide a method for preventing or reducing the putrefaction and fungal growth and microbial growth in alkyl glycoside aqueous solutions.

These and other objects, which will become apparent during the following detailed description, have been achieved by the inventors' discovery that the aforementioned problems can be overcome by maintaining an alkyl glycoside aqueous solution under specified conditions. The present invention has been accomplished on the basis of such a finding.

Particularly, the present invention provides an alkyl glycoside aqueous solution highly stable to microbial activities, which satisfies the following conditions (a) and/or (b):

(a) the solution has a pH value exceeding 7, and (b) the solution comprises a water soluble alcohol.

The alkyl glycoside aqueous solution of the present invention can prevent propagation of fungi easily and for a prolonged period of time, and can be applied to cosmetics in which applicable additives are restricted.

DETAILED DESCRIPTION OF THE PREFERRED EMBODIMENTS

Examples of the alkyl glycosides to be used in the present invention include compounds represented by the following general formula (I):

$$R^1(OR^2)_xG_y \qquad (I)$$

wherein $R^1$ is a straight or branched-chain alkyl, alkenyl or alkylphenyl group having 8 to 22 carbon atoms, each occurrence of $R^2$ within the $(OR^2)_x$ group is the same or different alkylene group having 2 to 4 carbon atoms, G is a reducing sugar residue having 5 to 6 carbon atoms, x indicates a mean value and is a number equal to 0 to 10 and y indicates a mean value and is a number equal to 1 to 10. Thus, the present alkyl glycosides include those in which $(OR^2)_x$ represents a homopolymer or a block or random copolymer of two or more different alkylene oxide units, such as, e.g., ethylene oxide, propylene oxide, isopropylene oxide, butylene oxide, or isobutylene oxide. In addition, the present alkyl glycosides may include mixtures of compounds having different values of x and y as well as different groups for $R^1$, $R^2$, and G.

The compound represented by the above general formula (I) can be obtained by generally known methods, for example by a process in which a sugar is directly reacted with a higher alcohol in the presence of an acid catalyst or by a process in which a sugar is reacted in advance with a lower alcohol such as methanol, ethanol, propanol, butanol or the like to obtain a lower alkyl glycoside which is then allowed to react with a higher alcohol (JP-B-47-24532 corresponding to U.S. Pat. No. 3,598,865, U.S. Pat. No. 3,839,318, European Patent No. 092,355, JP-A-58-189195, JP-A-59-139397 corresponding to U.S. Pat. No. 4,923,976). (The term "JP-B" as used herein means an "examined Japanese patent publication")

Examples of the higher alcohol to be used as a starting material for the alkyl glycoside synthesis include straight or branched-chain alkyl alcohols, alkenyl alcohols, alkylphenols, each of which having 8 to 22 carbon atoms, and alkylene oxide addition compounds of these three types of starting materials.

Examples of the sugar to be used as another starting material for the alkyl glycoside synthesis include monosaccharides, oligosaccharides, and polysaccharides. Illustrative examples of monosaccharides include: aldoses such as allose, altrose, glucose, mannose, gulose, idose, galactose, talose, ribose, arabinose, xylose, lyxose and the like; and ketoses such as fructose and the like. Illustrative examples of oligosaccharides include maltose, lactose, sucrose, maltotriose and the like. Illustrative examples of polysaccharides include hemicellulose, inulin, dextrin, dextran, xylan, starch, hydrolyzed starch and the like. Of these sugars, monosaccharides are particularly preferred as the starting material.

The alkyl glycoside aqueous solution of the present invention may contain an alkyl glycoside in an amount of from 10 to 80% by weight, preferably from 30 to 50% by weight, based on the total weight of the solution, as a pure substance. Amounts of the alkyl glycoside if smaller than 10% by weight would entail economical disadvantage and if larger than 80% by weight would cause increase in viscosity which is not preferable from handling point of view.

According to the present invention, an alkaline compound is added to the alkyl glycoside aqueous solution to maintain pH of the solution at a value exceeding 7. Examples of the alkaline compound include: inorganic alkaline compounds such as alkali metal hydroxides (e.g., sodium hydroxide, potassium hydroxide and the like) and alkali metal carbonates (e.g., sodium carbonate, potassium carbonate and the like); and organic alkaline compounds such as triethylamine, pyridine and the like; and mixtures thereof. Of these, a weak base, especially sodium carbonate, is particularly preferred. In this instance, an essential factor for the generation of proper antiseptic and fungicidal effects is not the amount of added alkaline compound but the pH value established by the addition of the compound. In other words, antiseptic and fungicidal effects can be maintained for a prolonged period of time by the use of a weak base compound having a buffer capacity.

The alkaline compound may be added in the form of solid or liquid as it is or as a solution, but preferably as its aqueous solution.

Examples of water-soluble alcohols eligible for use in the present invention include: monohydric alcohols such as methanol, ethanol, propanol, isopropanol, butanol, sec-butyl alcohol, tert-butyl alcohol and the like and polyhydric alcohols such as ethylene glycol, propylene glycol and the like. Among them, ethanol and isopropyl alcohol are preferred, and ethanol is particularly preferred.

According to the alkyl glycoside aqueous solution of the present invention, antiseptic and fungicidal effects can be attained either by maintaining the solution at a pH value higher than 7 with the addition of an alkaline compound or by adding a water-soluble alcohol to the solution. Practically, the alkyl glycoside aqueous solution may be maintained at a pH value of from 7 to 12, or a water-soluble alcohol may be added in an amount of from 0.1 to 30% by weight based on the total weight of the solution. Preferably, however, the alkaline compound and the water-soluble alcohol may be used jointly, in order to limit periodical changes in the appearance of the alkyl glycoside aqueous solution to a minimum and to ensure long-range stability of the solution.

When complete inhibition of microbial propagation is attempted only by the addition of an alkaline compound, it is necessary to adjust pH value of the solution to higher than 11. In such a case, the solution may preferably be maintained at a pH value of from 11 to 12. When complete inhibition of microbial propagation is attempted only by the addition of a water-soluble alcohol, it is necessary to use the alcohol in an amount of 10% or more by weight based on the total weight of the solution. In such a case, the alcohol may preferably be added in an amount of from 10 to 30% by weight based on the total weight of the solution. Such treatments are effective as an anti-microbe measure, but have a disadvantage in that large quantities of an alkaline compound and/or a water-soluble alcohol are required, in addition to a formulating limitation.

When used jointly, it is particularly preferred that pH value of the alkyl glycoside aqueous solution be adjusted to 9 to 11 by the addition of an alkaline compound (sodium carbonate, most preferably) before or after the addition of a water-soluble alcohol (ethanol, most preferably) in an amount of from 0.1 to 20% by weight, preferable from 0.1 to 5% by weight, based on the total weight of the solution.

The alkyl glycoside aqueous solution of the present invention can be used as a blending material of various cleaners for use in the cleaning of hair, clothes, dishes, the body and the like.

When used as a base material of a cleaner, the alkyl glycoside aqueous solution may be used preferably in an amount of from 1 to 80% by weight as effective amount of alkyl glycoside.

Such a cleaner composition may be mixed further with various components which include: generally used anionic surface active agents such as an alkylsulfuric ester, an alkylethersulfuric ester, an $\alpha$-olefin sulfonate, an alkyl sulfonate, a taurine-based surface active agent, a sarcosinate-based surface active agent, an isothionate-based surface active agent, an N-acyl acidic amino acid based surface active agent, a higher fatty acid salt, an acylated polypeptide and the like; ampholytic surface active agents such as an alkylbetaine type surface active agent, an amidopropylbetaine type surface active agent, an imidazoliniumbetaine type surface active agent, a sulfobetaine type surface active agent, a phosphobetaine type surface active agent, an amino acid type surface active agent (for example, sodium lauryl aminopropionate) and the like; nonionic surface active agents such as a coconut oil fatty acid diethanolamide, a stearic acid monoglyceride, lauryl dimethylamine oxide, a polyoxyethylene alkyl ether, a polyoxyethylene fatty acid ester, a sorbitan fatty acid ester, a polyoxyethylene sorbitan fatty acid ester and the like; cationic surface active agents such as stearyl trimethylammonium chloride, distearyl dimethylammonium chloride, an ethylsulfate lanolin fatty acid aminopropylethyldimetyl ammonium and the like; and generally used humidity keeping agents, thickeners, high polymer compounds (for example, carboxyethyl cellulose, hydroxyethyl cellulose, cationic cellulose and the like), perfumes, antiseptics and the like. Such surface active agents are well known in the art and are described in Kirk-Othmer, *Encyclopedia of Chemical Technology*, 3rd ed., vol. 22, John Wiley & Sons, pp. 322–432 (1983), incorporated herein by reference.

Other features of the invention will become apparent in the course of the following descriptions of exemplary embodiments which are given for illustration of the invention and are not intended to be limiting thereof.

EXAMPLES

In the examples, the evaluations of the antiseptic and fungicidal effects were made by the following tests.

Procedure

A cell suspension was prepared by suspending general bacteria and fungi in such a volume of sterile water that the cell density of the suspension reached $10^6$ to $10^7$ cells/ml ($10^4$ spores/ml as fungi). 1 ml of the cell suspension was added to 100 g of a sample, and the added cells were cultured by static culturing at 30° C. for 4 weeks, and then viable counts were measured in 1 g of the sample.

Evaluation

| Viable count | Evaluation (antiseptic and fungicidal effects) |
| --- | --- |
| less than 100 | — (yes, excellent) |
| 100 to 999 | – (yes, some) |
| 1000 or more | + (no) |

Inventive Examples 1 to 13 and Comparative Examples 1 and 2

A series of samples were prepared by adding various antiseptic and fungicidal compounds to an aqueous solution of dodecyl glucoside (30% by weight as pure substance) as shown in Table 1, and the effects of the compounds were judged based on the above tests. The results are shown in Table 1.

TABLE 1

| Example No. | Additive Agents Name/Amount* | Solution pH | Effect Judged |
| --- | --- | --- | --- |
| Inventive | | | |
| 1 | NaOH 0.05% | 9.0 | – |
| 2 | NaOH 0.1% | 10.0 | – |
| 3 | NaOH 0.15% | 11.0 | — |
| 4 | KOH 0.15% | 11.0 | — |
| 5 | Na$_2$CO$_3$ 0.15% | 9.5 | – |
| 6 | Ethanol 4% | 7.0 | – |
| 7 | Ethanol 10% | 7.0 | — |
| 8 | Propanol 4% | 7.0 | – |
| 9 | NaOH 0.03%, Ethanol 4% | 8.0 | – |
| 10 | NaOH 0.05%, Ethanol 4% | 9.0 | — |
| 11 | NaOH 0.1%, Ethanol 4% | 10.0 | — |
| 12 | NaOH 0.05%, Ethanol 2% | 9.0 | – |
| 13 | NaOH 0.05%, Ethanol 3% | 9.0 | — |
| Comparative | | | |
| 1 | sodium benzoate 1.5% | 7.0 | + |
| 2 | no addition | 7.0 | + |

*: % by weight based on the total weight of the alkyl glycoside aqueous solution after addition of the additive agent

Inventive Examples 14 to 16 and Comparative Example 3

A series of samples were prepared by adding various antiseptic and fungicidal compounds to an aqueous solution of decyl glucoside (40% by weight as pure substance) as shown in Table 2, and the effects of the compounds were judged based on the above tests. In this instance, the test samples were stored at 40° C. for one month prior to the addition of cell suspension, in order to examine periodical changes in the antiseptic and fungicidal effects. The results are shown in Table 2.

TABLE 2

| Example No. | Additive Agents Name/Amount* | pH at the Time of Preparation | pH After 1 Month at 40° C. | Effect Judged |
| --- | --- | --- | --- | --- |
| Inventive | | | | |
| 14 | NaOH 0.07%, Ethanol 2.5% | 9.5 | 8.7 | – |
| 15 | Na$_2$CO$_3$ 0.15%, Ethanol 2.5% | 9.5 | 9.3 | — |
| 16 | Na$_2$CO$_3$ 0.2%, Ethanol 2.5% | 10.0 | 9.7 | — |
| Comparative | | | | |
| 3 | no addition | 0 | 6.8 | + |

*: % by weight based on the total weight of the alkyl glycoside aqueous solution after addition of the additive agent

Inventive Examples 17 to 25

In order to examine antiseptic and fungicidal effects more in detail, a series of samples were prepared by adding various antiseptic and fungicidal compounds to an aqueous solution of decyl glucoside (40% by weight as pure substance) as shown in Table 3, and the effects of the compounds were examined in terms of a relationship between culturing days (after 1, 3 and 7 days and 4 weeks) and viable counts. The results of the tests are shown in Table 3.

TABLE 3

| Example No. | Additive Agents Name/Amount* | Solution pH | Effects Judged After 1 Days | 3 Days | 7 Days | 4 Weeks |
| --- | --- | --- | --- | --- | --- | --- |
| 17 | Na$_2$CO$_3$ 0.15%, Ethanol 2.5% | 9.5 | — | — | — | — |
| 18 | Na$_2$CO$_3$ 0.25%, Ethanol 2.5% | 10.0 | — | — | — | — |
| 19 | Na$_2$CO$_3$ 0.78%, Ethanol 2.5% | 10.5 | — | — | — | — |
| 20 | NaOH 0.05% | 9.0 | + | + | + | – |
| 21 | NaOH 0.1% | 10.0 | – | – | – | – |
| 22 | NaOH 0.15% | 11.0 | — | — | — | — |
| 23 | Ethanol 2.5% | 7.0 | + | + | + | – |
| 24 | Ethanol 4% | 7.0 | + | + | + | – |
| 25 | Ethanol 10% | 7.0 | + | + | – | — |

*: % by weight based on the total weight of the alkyl glycoside aqueous solution after addition of the additive agent Thus, it is apparent that there has been provided, in accordance with the present invention, an alkyl glycoside aqueous solution which is highly stable to microbial activities, such as microbial growth and degradation, and is useful as a surface active agent. The alkyl glycoside aqueous solution of the present invention is characterized in that its pH is maintained at a value exceeding 7 by the addition of an alkaline compound and/or it contains a water soluble alcohol, thereby exerting markedly excellent antiseptic and fungicidal properties for a prolonged period of time.

While the invention has been described in detail and with reference to specific embodiments thereof, it will be apparent to one skilled in the art that various changes and modifications can be made therein without departing from the spirit and scope thereof.

What is claimed as new and desired to be secured by Letters Patent of the United States is:

1. An alkyl glycoside aqueous solution consisting essentially of
   a) 30–50% by weight of $C_{10}$–$C_{12}$ alkyl glycosides;
   b) water; and
   c) 2–5% by weight of a water soluble alcohol selected from the group consisting of methanol, ethanol, propanol, isopropanol, butanol, sec-butyl alcohol, tert-butyl alcohol, ethylene glycol, and propylene glycol; said solution having a pH of from 9 to 11.

2. The alkyl glycoside aqueous solution as claimed in claim 1, wherein said water-soluble alcohol is selected from the group consisting of ethanol, isopropyl alcohol, and mixtures thereof.

3. The alkyl glycoside aqueous solution as claimed in claim 1, wherein said water-soluble alcohol is ethanol.

4. The aqueous solution as claimed in claim 3, wherein said solution has a pH of from 9–10.

5. The alkyl glycoside aqueous solution as claimed in claim 1 wherein said component a) alkyl glycosides are selected from the group consisting of decyl glycoside and dodecyl glycoside.

6. The aqueous solution as claimed in claim 1, comprising 2–4% by weight c).

7. The aqueous solution as claimed in claim 6, wherein said solution has a pH of from 9–10 and wherein said alcohol is ethanol.

8. The aqueous solution as claimed in claim 1, wherein said water-soluble alcohol is selected from the group consisting of ethanol and isopropanol.

9. The aqueous solution as claimed in claim 1, wherein said solution has a pH of from 9–10.

10. An alkyl glycoside aqueous solution consisting essentially of
    a) 30 to 50% by weight of an alkyl glycoside of the formula (I):

$$R^1 G_y$$

wherein $R^1$ is a straight or branched-chain alkyl having 10 to 12 carbon atoms, G is a reducing sugar residue having 5 to 6 carbon atoms and y indicates a mean value and is a number equal to 1 to 3;
    b) water; and
    c) 2–5% by weight of a water-soluble alcohol selected from the group consisting of methanol, ethanol, propanol, isopropanol, butanol, sec-butyl alcohol, tert-butyl alcohol, ethylene glycol, and propylene glycol; said solution having a pH of from 9 to 11.

11. The aqueous solution as claimed in claim 10, comprising 2–4% by weight c).

12. The aqueous solution as claimed in claim 11, wherein said solution has a pH of from 9–10 and wherein said alcohol is ethanol.

13. The aqueous solution as claimed in claim 10, wherein said alcohol is ethanol.

14. The aqueous solution as claimed in claim 13, wherein said solution has a pH of from 9–10.

15. The aqueous solution as claimed in claim 10, wherein said water-soluble alcohol is selected from the group consisting of ethanol and isopropanol.

16. The aqueous solution as claimed in claim 10, wherein said solution has a pH of from 9–10.

* * * * *